US010576285B2

(12) United States Patent
Annoni et al.

(10) Patent No.: US 10,576,285 B2
(45) Date of Patent: Mar. 3, 2020

(54) METHOD AND APPARATUS FOR CONTROLLING SPINAL CORD STIMULATION TO TREAT HYPERTENSION

(71) Applicant: Boston Scientific Neuromodulation Corporation, Valencia, CA (US)

(72) Inventors: Elizabeth Mary Annoni, White Bear Lake, MN (US); Kyle Harish Srivastava, Saint Paul, MN (US); Craig Stolen, New Brighton, MN (US); Pramodsingh Hirasingh Thakur, Woodbury, MN (US); Bradley Lawrence Hershey, Valencia, CA (US); Stephen B. Ruble, Lino Lakes, MN (US); William Conrad Stoffregen, Lake Elmo, MN (US); Bryan Allen Clark, Forest Lake, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 101 days.

(21) Appl. No.: 15/812,788

(22) Filed: Nov. 14, 2017

(65) Prior Publication Data

US 2018/0133480 A1 May 17, 2018

Related U.S. Application Data

(60) Provisional application No. 62/421,758, filed on Nov. 14, 2016.

(51) Int. Cl.
*A61N 1/36* (2006.01)
*A61N 1/05* (2006.01)
(Continued)

(52) U.S. Cl.
CPC ...... *A61N 1/36117* (2013.01); *A61B 5/02255* (2013.01); *A61N 1/056* (2013.01);
(Continued)

(58) Field of Classification Search
CPC . A61B 5/0024; A61B 5/0031; A61B 5/02158; A61B 5/02255; A61N 1/0551;
(Continued)

(56) References Cited

U.S. PATENT DOCUMENTS

| 5,824,021 A | 10/1998 | Rise |
| 7,218,964 B2 | 5/2007 | Hill et al. |

(Continued)

FOREIGN PATENT DOCUMENTS

| WO | WO-2007007058 A1 | 1/2007 |
| WO | WO-2018089981 A1 | 5/2018 |

OTHER PUBLICATIONS

"International Application Serial No. PCT/US2017/061476, International Preliminary Report on Patentability dated May 23, 2019", 8 pgs.

(Continued)

*Primary Examiner* — George Manuel
(74) *Attorney, Agent, or Firm* — Schwegman Lundberg & Woessner, P.A.

(57) ABSTRACT

An example of a system for modulating blood pressure may include a blood pressure monitoring circuit, a blood pressure modulation device, and a control circuit. The blood pressure monitoring circuit may be configured to sense signals and generate one or more blood pressure parameters indicative of the blood pressure and/or a vascular resistance and one or more activity parameters indicative of an activity level and/or a postural change using the sensed signals. The blood pressure modulation device may be configured to deliver a therapy modulating the blood pressure. The control circuit may be configured to control the therapy using therapy parameters, receive the one or more blood pressure parameters and the one or more activity parameters, analyze changes in the one or more blood pressure parameters that
(Continued)

are correlated to changes in the one or more activity parameters, and adjust the therapy parameters using an outcome of the analysis.

20 Claims, 4 Drawing Sheets

(51) Int. Cl.
*A61N 1/365* (2006.01)
*A61B 5/0225* (2006.01)
*A61B 5/00* (2006.01)
*A61B 5/0215* (2006.01)

(52) U.S. Cl.
CPC ....... *A61N 1/0551* (2013.01); *A61N 1/36053* (2013.01); *A61N 1/36114* (2013.01); *A61N 1/36564* (2013.01); *A61B 5/0024* (2013.01); *A61B 5/0031* (2013.01); *A61B 5/02158* (2013.01); *A61N 1/36031* (2017.08)

(58) Field of Classification Search
CPC ................ A61N 1/056; A61N 1/36031; A61N 1/36053; A61N 1/36114; A61N 1/36117; A61N 1/36564
See application file for complete search history.

(56) References Cited

U.S. PATENT DOCUMENTS

| | | | |
|---|---|---|---|
| 7,542,803 B2 | 6/2009 | Heruth et al. | |
| 7,769,464 B2 | 8/2010 | Gerber et al. | |
| 7,822,481 B2 | 10/2010 | Gerber et al. | |
| 7,957,809 B2 | 6/2011 | Bourget et al. | |
| 8,868,188 B2 | 10/2014 | Hershey | |
| 2003/0216792 A1 | 11/2003 | Levin et al. | |
| 2005/0149131 A1 | 7/2005 | Libbus et al. | |
| 2007/0027497 A1* | 2/2007 | Parnis ................ | A61N 1/36114 607/45 |
| 2007/0142864 A1 | 6/2007 | Libbus et al. | |
| 2008/0009917 A1 | 1/2008 | Rossing et al. | |
| 2013/0018438 A1* | 1/2013 | Chow ................. | A61N 1/3787 607/60 |
| 2013/0296965 A1 | 11/2013 | Mokelke et al. | |
| 2015/0196766 A1 | 7/2015 | Rosenberg et al. | |

OTHER PUBLICATIONS

"International Application Serial No. PCT/US2017/061476, International Search Report dated Jan. 22, 2018", 5 pgs.

"International Application Serial No. PCT/US2017/061476, Written Opinion dated Jan. 22, 2018", 6 pgs.

Bath, Eva, et al., "Effects of Dynamic and Static Neck Suction on Muscle Nerve Sympathetic Activity, Heart Rate and Blood Pressure in Man", J. Physiol, (1981), 551-564.

Calhoun, David A., et al., "Resistant Hypertension: Diagnosis, Evaluation, and Treatment—A Scientific Statement From the American Heart Association Professional Education Committee of the Council for High Blood Pressure Research", Circulation, (Jan. 24, 2008), e510-e526.

Egan, Brent M., et al., "Uncontrolled and Apparent Treatment Resistant Hypertension in the United States, 1988 to 2008", Circulation, 124, (Aug. 8, 2011), 1046-1058.

Fields, Larry E., et al., "The Burden of Adult Hypertension in the United States 1999 to 2000", Hypertension, (Aug. 23, 2004), 398-404.

James, Paul A., et al., "2014 Evidence-Based Guideline for the Management of High Blood Pressure in Adults Report From the Panel Members Appointed to the Eighth Joint National Committee (JNC 8)", Journal of the American Medical Association, 311 (5), (Dec. 18, 2013), 507-520.

Klaus, D., "Differential Treatment of Exercise Hypertension", Herz Nr.2, (1987), 146-155.

Lalande, Sophie, et al., "Diastolic Dysfunction: A Link Between Hypertension and Heart Failure", Drugs Today (Barc), 44 (7), (Jul. 2008), 503-513.

Masuo, Kazuko, et al., "Changes in Frequency of Orthostatic Hypotension in Elderly Hypertensive Patients Under Medications", American Journal of Hypertension, vol. 9, No. 3, (Mar. 1996), 263-268.

Van Iterson, Erik H., et al., "Intrathecal fentanyl blockade of afferent neural feedback from skeletal muscle during exercise in heart failure patients: Influence on circulatory power and pulmonary vascular capacitance", International Journal of Cardiology 201, (Aug. 14, 2015), 384-393.

Victor, Ronald G., et al., "Differential Control of Heart Rate and Sympathetic Nerve Activity during Differential Control of Heart Rate and Sympathetic Nerve Activity during Dynamic Exercise—Insight from Intraneural Recordings in Humans", J. Clin Invest, vol. 79, (Feb. 1987), 508-516.

\* cited by examiner

METHOD AND APPARATUS FOR CONTROLLING SPINAL CORD STIMULATION TO TREAT HYPERTENSION

CLAIM OF PRIORITY

This application claims the benefit of priority under 35 U.S.C. § 119(e) of U.S. Provisional Patent Application Ser. No. 62/421,758, filed on Nov. 14, 2016, which is herein incorporated by reference in its entirety.

TECHNICAL FIELD

This document relates generally to medical devices and more particularly to a system for device-based hypertension treatment with closed-loop control.

BACKGROUND

Hypertension, or high blood pressure, affects millions of Americans and is known to be the strongest risk factor for developing cardiovascular disease. Chronic hypertension can lead to cardiac remodeling due to increased load on a patient's heart and can increase the patient's risk of developing heart failure. For about 20-30% of hypertensive patients, common pharmaceutical approaches are unable to control the rise in arterial blood pressure. For these patients, a device-based approach can be used to control blood pressure. One approach for reducing blood pressure is to target the imbalance in the autonomic nervous system often seen in hypertensive patients. This imbalance manifests as an over activation of the sympathetic nervous system and a withdrawal of the parasympathetic nervous system.

For example, muscle activation such as during postural change or exercise can cause increased sympathetic activity, thereby elevating the blood pressure. Exercise pressor reflex (neurological reflex that constricts arterioles during exercise) may raise the systolic blood pressure of a hypertensive patient to over 200 mmHg. This differs from chronic hypertension, which is marked by baseline systolic blood pressure levels above 140 mmHg. The exercise pressor reflex is particularly problematic for patients who would use exercise to improve their blood pressure. These large spikes in blood pressure can result in cardiovascular, cerebrovascular, and/or organ damage. Proper treatment requires the ability to adapt as activity levels and blood pressure fluctuates. Research into this mechanism has been conducted using fentanyl injections, which blocks sympathetic afferent nerves in the spinal cord to reduce blood pressure during exercise in heart failure patients.

In a hypertensive patient, a persistent increase in blood pressure can result in desensitization of arterial baroreceptors, which can lead to development of orthostatic hypotension. The patient experiences hypertension while in a supine position, but has orthostatic intolerance during a postural transition. This makes the treatment challenging because treating one condition could worsen the other. Such patients can benefit from a treatment option that can reduce blood pressure in a hypertensive state and increase blood pressure when the patient becomes hypotensive, such as during postural changes. For example, a therapy that reduces hypertension can be enabled during the hypertensive state and inhibited during the hypotensive state, or a therapy that heightens the blood pressure can be delivered during the hypotensive state.

SUMMARY

An example (e.g., "Example 1") of a system for modulating blood pressure of a patient may include a blood pressure monitoring circuit, a blood pressure modulation device, and a control circuit. The blood pressure monitoring circuit may be configured to sense signals from the patient and to generate one or more blood pressure parameters and one or more activity parameters using the sensed signals. The one or more blood pressure parameters are indicative of one or more of a blood pressure or a vascular resistance of the patient. The one or more activity parameters are indicative of one or more of an activity level or a postural change of the patient using the sensed signals. The blood pressure modulation device may be configured to deliver a therapy modulating the blood pressure. The control circuit may be configured to control the therapy using therapy parameters, to receive the one or more blood pressure parameters and the one or more activity parameters, to analyze changes in the one or more blood pressure parameters that are correlated to changes in the one or more activity parameters, and to adjust the therapy parameters using an outcome of the analysis.

In Example 2, the subject matter of Example 1 may optionally be configured such that the blood pressure monitoring circuit is further configured to receive one or more user commands, and the control circuit is further configured to incorporate the received one or more user commands into the analysis of the changes in the one or more blood pressure parameters that are correlated to the changes in the one or more activity parameters.

In Example 3, the subject matter of any one or any combination of Examples 1 and 2 may optionally be configured such that the control circuit is further configured to optimize the therapy parameters by executing an optimization algorithm for an optimal therapeutic effect as indicated by the one or more blood pressure parameters and the one or more activity parameters.

In Example 4, the subject matter of Example 1 may optionally be configured such that the control circuit is further configured to allow for calibration of the optimization algorithm in response to the optimal therapeutic effect falling outside a specified threshold.

In Example 5, the subject matter of any one or any combination of Examples 3 and 4 may optionally be configured such that the control circuit is further configured to allow for calibration of the optimization algorithm in response to a user command for calibration.

In Example 6, the subject matter of any one or any combination of Examples 1 to 5 may optionally be configured to further include a power management circuit configured to control a power mode of the system. The power management circuit is configured to place the system in a low-power mode while the patient is sleeping, as indicated by one or more of the one or more activity parameters or a user command indicating a patient-specified sleeping period.

In Example 7, the subject matter of any one or any combination of Examples 1 to 6 may optionally be configured to include an implantable medical device configured to be placed within the patient. The implantable medical device includes the blood pressure modulation device, the control circuit, and at least a portion of the blood pressure monitoring circuit.

In Example 8, the subject matter of Example 7 may optionally be configured such that the blood pressure monitoring circuit includes an intravascular blood pressure sensor configured to directly sense the blood pressure.

In Example 9 the subject matter of any one or any combination of Examples 7 and 8 may optionally be configured such that the blood pressure monitoring circuit includes an extravascular physiological sensor configured to indirectly sense the blood pressure using a surrogate of the blood pressure.

In Example 10, the subject matter of any one or any combination of Examples 7 to 9 may optionally be configured such that the blood pressure monitoring circuit includes a physiological sensor configured to sense a signal indicative of the vascular resistance.

In Example 11, the subject matter of any one or any combination of Examples 7 to 10 may optionally be configured such that the blood pressure monitoring circuit includes an activity sensor configured to sense the one or more of the activity level or the postural change.

In Example 12, the subject matter of Example 11 may optionally be configured such that the activity sensor includes an accelerometer.

In Example 13, the subject matter of any one or any combination of Examples 11 and 12 may optionally be configured such that the activity sensor includes a gyroscope.

In Example 14, the subject matter of any one or any combination of Examples 7 to 13 may optionally be configured such that the implantable medical device includes an implantable neuromodulator, and the blood pressure modulation device includes a neuromodulation device configured to deliver a spinal cord stimulation (SCS).

In Example 15, the subject matter of Example 14 may optionally be configured to further include an implantable lead configured to be connected to the implantable neuromodulator. The implantable lead including electrodes is configured for delivering the SCS and at least one sensor of the blood pressure monitoring circuit.

An example (e.g., "Example 16") of a method for modulating blood pressure of a patient is also provided. The method may include sensing signals from the patient, generating parameters using the sensed signals. The parameters may include one or more blood pressure parameters indicative of one or more of the blood pressure or a vascular resistance of the patient and one or more activity parameters indicative of one or more of an activity level or a postural change of the patient. The method may further include analyzing changes in the one or more blood pressure parameters correlated to changes in the one or more activity parameters, adjusting therapy parameters using an outcome of the analysis, controlling a therapy modulating the blood pressure using the therapy parameters, and delivering the therapy to the patient.

In Example 17, the subject matter of Example 16 may optionally further include receiving one or more user commands and incorporating the one or more user commands into the analysis of the changes in the one or more blood pressure parameters correlated to the changes in the one or more activity parameters.

In Example 18, the subject matter of any one or any combination of Examples 16 and 17 may optionally further include approximately optimizing the therapy parameters by executing an optimization algorithm. The optimization algorithm allows the therapy parameters to be set for an approximately optimal therapeutic effect as indicated by the one or more blood pressure parameters and the one or more activity parameters.

In Example 19, the subject matter of delivering the therapy as found in any one or any combination of Examples 16 to 18 may optionally include delivering spinal cord stimulation (SCS) using an implantable medical device.

In Example 20, the subject matter of sensing the signals as found in Example 19 may optionally include sensing the signals using implantable sensors contained in or connected to the implantable medical device.

In Example 21, the subject matter of sensing the signals as found in any one or any combination of Examples 16 to 20 may optionally include sensing the blood pressure using an intravascular blood pressure sensor.

In Example 22, the subject matter of sensing the signals as found in any one or any combination of Examples 16 to 21 may optionally include sensing an extravascular signal as a surrogate for the blood pressure.

In Example 23, the subject matter of sensing the extravascular signal as found in Example 22 may optionally include sensing a heart sound signal indicative of heart sounds of the patient.

In Example 24, the subject matter of sensing the extravascular signal as found in any one or any combination of Examples 22 and 23 may optionally include sensing a photoplethysmographic signal.

In Example 25, the subject matter of sensing the extravascular signal as found in any one or any combination of Examples 22 and 23 may optionally include sensing an impedance signal.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
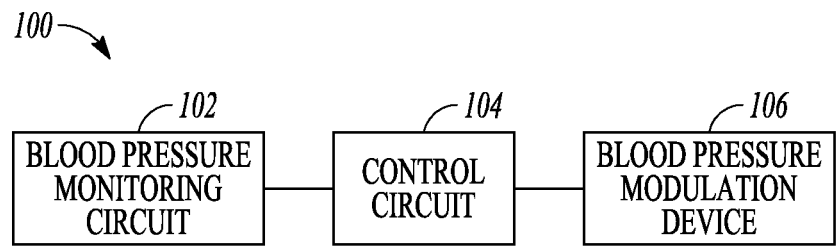
FIG. 1 illustrates an embodiment of a system for modulating blood pressure.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a closed-loop, device-based therapy system for treating hypertension, including various sensors and signals providing for feedback control and therapy optimization. Research has suggested that dynamic changes in blood pressure are associated with peroneal nerve activity. Electrical stimulation targeted at such pathways can reduce blood pressure specifically during dynamic swings associated with the exercise pressor reflex. Such electrical stimulation is likely to reduce sympathetic tone and subsequently dilate peripheral vessels in order to reduce blood pressure. An example of the closed-loop, device-based therapy system for treating hypertension includes a spinal cord stimulation (SCS) system. Other examples of device-based therapy system for treating hypertension includes systems for delivering dorsal root ganglia stimulation, sympathetic chain modulation, and peripheral sympathetic nerve modulation.

SCS has been applied in treating pain and cardiovascular diseases including hypertension. Beneficial effects of SCS in a patient may vary over time based on physiological or lifestyle changes of the patient. Thus, parameters controlling delivery of the SCS should be dynamically adjusted or optimized to accommodate for these changes. Examples of such parameters include electrode configuration, pulse frequency (or inter-pulse interval), pulse width, and pulse amplitude. The stimulation paradigm can also be changed as needed. However, changes in SCS parameters and paradigms may require an authorized, trained professional user to reprogram device settings. Such a reprogramming can optimize the SCS parameters and paradigms for the short term, but many adjustments are likely needed for the long term.

Thus, there is a need for a closed-loop system that delivers SCS to treat a patient's hypertension and automatically optimizes the delivery of the SCS using one or more signals indicative of the patient's instant blood pressure in real time. In one example, a patient has elevated exercise pressor reflex, so a desirable treatment option is to react to dynamic swings in the patient's blood pressure and enable the therapy when it is needed by the patient. In another example, a patient is supine hypertensive and experiences orthostatic intolerance, so it is desirable to enable the therapy only when it is needed by the patient, to improve the patient's blood pressure response to postural transitions. In another example, the closed-loop system can provide for battery management to extend battery life by delivering therapy only when it is needed, when the therapy is delivered by a battery-powered device, such as an implantable device.

The present closed-loop system can include a therapy device to deliver one or more therapies for modulating blood pressure and one or more sensors to monitor one or more signals indicative of blood pressure. In one embodiment, the therapy device includes a chronically implanted neuromodulation device to deliver SCS. The one or more signals are processed to extract information indicative of a need for delivering stimuli that modulate the blood pressure. In various embodiments, the system can detect onset of the exercise pressor reflex and treats its effects by delivering SCS to substantially reduce damaging effects of high blood pressure on the cardiovascular system. In various embodiments, the system can modulate or optimize stimulation parameters and provide as-needed SCS therapy based on the activity of the patient. In various embodiments, the system executes an algorithm that automatically determines an optimal therapy for a given physiological parameter. The optimization of the therapy can include adjusting stimulation parameters such as electrode configuration, pulse waveform shape, pulse frequency, duty cycle, pulse width, and pulse amplitude, and can also include adjusting stimulation paradigms such as kilohertz frequency stimulation and burst stimulation. While SCS is discussed as a specific example, the monitoring of blood pressure according to the present subject matter can be used for controlling any type of device for delivering a therapy that modulates blood pressure of the patient.

FIG. 1 illustrates an embodiment of a system 100 for modulating blood pressure of a patient. System 100 can include a blood pressure monitoring circuit 102, a blood pressure modulating device 106, and a control circuit 104. Blood pressure monitoring circuit 102 can sense signals from the patient and generate one or more physiological parameters and optionally one or more functional parameters using the sensed signals. The one or more physiological parameters can include one or more blood pressure parameters indicative of one or more of the blood pressure or a vascular resistance of the patient, and optionally one or more activity parameters indicative of one or more of an activity level or a postural change of the patient. The one or more functional parameters can include one or more activity parameters indicative of one or more of the activity level or the postural change of the patient. Thus, in various embodiments, blood pressure monitoring circuit 102 can generate one or more blood pressure parameters and one or more activity parameters. The one or more blood pressure parameters are one or more physiological parameters, while the one or more activity signal can include one or more physiological parameters and/or one or more functional parameters. Blood pressure modulation device 106 can deliver a therapy modulating the blood pressure. Example of such a therapy include an SCS, dorsal root ganglia stimulation, sympathetic chain modulation, and peripheral sympathetic nerve modulation. Control circuit 104 can control the therapy using therapy parameters, receive the one or more blood pressure parameters and the one or more activity parameters, analyze changes in the one or more blood pressure parameters correlated to changes in the one or more activity parameters, and adjust the therapy parameters using an outcome of the analysis.

In various embodiments, circuits of system 100, including various embodiments of its components discussed in this document, may be implemented using a combination of hardware and software. For example, blood pressure monitoring circuit 102, including its various embodiments discussed in this document, and control circuit 104 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
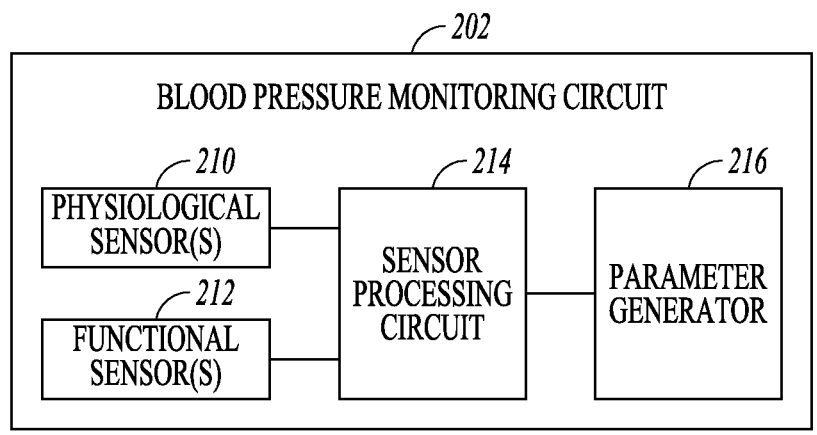
FIG. 2 illustrates an embodiment of a blood pressure monitoring circuit, such as may be used in the system of FIG. 1.

FIG. 2 illustrates an embodiment of a blood pressure monitoring circuit 202, which represent an example of blood pressure monitoring circuit 102. Blood pressure monitoring circuit 202 can include one or more physiological sensors 210, one or more functional sensors 212 (if needed), a sensor processing circuit 214, and a parameter generator 216.

Physiological sensor(s) 210 can sense one or more physiological signals each indicative of a physiological function or state of the patient. In various embodiments, physiological sensor(s) 210 can each be an invasive sensor (e.g., implantable sensor) or a non-invasive sensor (a wearable sensor). In various embodiments, one or more physiological signals include one or more signals indicative one or more of a blood pressure or a vascular resistance of the patient. In various embodiments, one or more physiological signals can also include one or more signals indicative one or more of an activity level or a posture change of the patient. In various embodiments, physiological sensor(s) 210 can include one or more sensors selected from the following examples (1)-(7):

(1) A blood pressure sensor to sense a blood pressure or a surrogate of the blood pressure of the patient and produce a blood pressure signal indicative of the blood pressure. The blood pressure sensor can be an intravascular sensor to sense the blood pressure directly or an extravascular sensor to sense the surrogate of the blood pressure. Examples of the blood pressure sensor include:
  a. an invasive arterial pressure sensor to be placed in an artery to sense an arterial blood pressure being a direct measure of an arterial blood pressure;
  b. a non-invasive blood pressure cuff to sense an external blood pressure;
  c. a heart sound sensor to sense a heart sound signal indicative of at least second heart sounds (S2), such as an accelerometer or a microphone, in an implantable device or incorporated into the distal end of a lead connected to the implantable device;
  d. a photoplethysmography (PPG) sensor to sense a PPG signal;
  e. an impedance sensor to sense an impedance signal indicative of the blood pressure or the vascular resistance, such as an electrical bioimpedance sensor to sense an electrical bioimpedance signal or an impedance cardiography sensor to sense an impedance cardiographic signal (noninvasive measurement of electrical impedance of the thorax);
  f. a neural sensor to sense a nerve signal indicative of sympathetic tone (which in turn indicates blood pressure), such as electrode(s) incorporated into the distal end of a lead connected to the implantable device to sense local field potentials and/or evoked compound action potentials; and
  g. a sensor to sense an electroencephalographic (EEG) signal indicative of activity or the sympathetic tone.
(2) Cardiac sensing electrodes to sense a cardiac signal allowing for detection of heart rate and heart rate variability (HRV).
(3) A respiratory sensor to sense a respiratory signal indicative of respiratory rate.
(4) A galvanic skin response (GSR) sensor to sense a GSR signal indicative of sweating.
(5) Electromyogram (EMG) sensing electrodes to sense an EMG signal indicative of muscle activation.
(6) A peripheral vascular sensor to sensor one or more of peripheral perfusion or vascular resistance, such as a flow sensor, a perfusion sensor; and a temperature sensor.
(7) A chemical sensor to sense one or more chemical biomarkers of exertion, such as one or more of lactate or interleukin 6 (IL-6).

Functional sensor(s) 212, when needed, can sense one or more functional signals each indicative of a physical activity or state of the patient. In various embodiments, functional sensor(s) 212 can each be an invasive sensor (e.g., implantable sensor) or a non-invasive sensor (e.g., wearable sensor). In various embodiments, the one or more functional signals are indicative of one or more of an activity level or a postural change of the patient. In various embodiments, functional sensor(s) 212 can include an activity sensor to sense one or more of activity or postural change of the patient, and can produce an activity signal indicative of one or more of an activity level or a postural change. Examples of such an activity sensor include one or more of an accelerometer or a gyroscope. The accelerometer can sense the activity and/or the postural change of the patient, and can produce an accelerometer signal indicative of the activity level and/or postural change. The gyroscope can sense angular acceleration indicative of angular postural change (in roll, pitch, and yaw) of the patient, and can produce a gyroscope signal indicative of the angular postural change.

Sensor processing circuit 214 can process the one or more physiological signals produced by physiological sensor(s) 210 and the one or more functional signals produced by functional sensor(s) 212. In various embodiments, the processing can include signal conditioning and detection of signal features (e.g., heart sounds and cardiac depolarizations allowing for measurement of parameters).

Parameter generator 216 can generate one or more physiological parameters each indicative of the physiological function or state of the patient using the processed one or more physiological signals, and can generate one or more functional parameters each indicative of the physical activity or state of the patient using the processed one or more functional signals. In various embodiments, the one or more physiological parameters can include one or more blood pressure parameters indicative of one or more of a blood pressure or a vascular resistance of the patient, and optionally one or more activity parameters indicative of one or more of an activity level or a postural change of the patient. The one or more functional parameters can include one or more activity parameters indicative of one or more of an activity level or a postural change of the patient. In one embodiment, parameter generator 216 generates at least one physiological parameter being a blood pressure parameter and at least one physiological parameter being an activity parameter. In another embodiment, parameter generator 216 generates at least one physiological parameter being a blood pressure parameter and at least one functional parameter being an activity parameter.

These parameters allow for analysis of correlation between the activity level and/or the postural change and changes in the blood pressure and/or vascular resistance. In various embodiments, the one or more physiological parameters can include one or more blood pressure parameters each indicative of one or more of the blood pressure or the vascular resistance. The one or more blood pressure parameters can each be a direct measure of a blood pressure or a surrogate for the blood pressure, and can include one or more parameters selected from the following examples (1)-(6):

(1) An arterial pressure measured from the arterial blood pressure signal.
(2) A blood pressure measured from the external blood pressure signal.
(3) A heart sound parameter measured from the heart sound signal, such as a parameter measured from S2 in the heart sound signal. S2 can be used as an indirect measure of the blood pressure).
(4) A PPG parameter measured from the PPG signal, such as pulse transit time, pulse amplitude, pulse volume, systolic pressure, and/or diastolic pressure.

(5) A hemodynamic parameter indicative of blood pressure or vascular resistance measured from the electrical bioimpedance signal or the impedance cardiographic signal.

(6) A parameter being a measure of the sympathetic tone measuring from the nerve signal or the EEG signal.

The one or more physiological parameters can also include one or more activity parameters each indicative of one or more of the activity level or the postural change. Such one or more activity parameters (each being a physiological parameter) can include one or more parameters selected from the following examples (1)-(6):

(1) A heart rate and/or an HRV parameter measured from the cardiac signal. Time and frequency domain measures of the heart rate and HRV can be used to detect exertion. HRV is the beat-to-beat variance in cardiac cycle length over a period of time. An "HRV parameter" as used in this document includes any parameter being a measure of the HRV, including any qualitative expression of the beat-to-beat variance in cardiac cycle length over a period of time. Examples of the HRV parameters include standard deviation of normal-to-normal intervals (SDNN), standard deviation of averages of normal-to-normal intervals (SDANN), ratio of low-frequency (LF) HRV to high-frequency (HF) HRV (LF/HF ratio), HRV footprint, root-mean-square of successive differences (RMSSD), and percentage of differences between normal-to-normal intervals that are greater than 50 milliseconds (pNN50). The HRV can also include a measure for respiratory sinus arrhythmia (RSA), which is essentially a short-term HRV measure.

(2) A respiration rate measured from the respiratory signal. The respiratory rate increases with increased sympathetic activation or increased exertion. Respiration can also be used to analyze autonomic tone through respiration sinus arrhythmia.

(3) A GSR parameter indicative of sweating, measured from the GSR signal. Sweating due to increased activity can lead to reduced resistance and increased skin conductivity. GSR also provides a measure of autonomic tone with increased sympathetic activity causing in increase in skin conductance. Time domain measures for mean skin conductance and the number of skin conductance fluctuations can be measured are examples of GSR measures.

(4) A muscular activity parameter measured from the EMG. Pattern analysis, time domain (amplitude, latency, etc.) measures, and frequency domain measures can be used to detect muscle activation. Muscle activation during exercise increases sympathetic tone and blood pressure via the exercise pressor response.

(5) A peripheral vascular parameter measured from the peripheral vascular signal and indicative of perfusion and vascular resistance in peripheral blood vessels.

(6) An exertion parameter measured using the chemical biomarkers and indicative of changes in exertion.

In various embodiments, the one or more functional parameters can include one or more activity parameters each indicate one or more of the activity level or the postural change. Such one or more activity parameters (each being a functional parameter) can include one or more parameters selected from the following examples (1) and (2):

(1) an activity parameter indicative of the activity level of the patient, measured using the accelerometer signal, to correlate changes in the physiological parameter indicative of the blood pressure or the vascular resistance of the patient to changes in the patient's activity level; and (2) a postural parameter indicative of the postural change of the patient, measured using the gyroscope signal and/or the accelerometer signal, to correlate changes in the physiological parameter indicative of the blood pressure or the vascular resistance of the patient to changes in the postural change of the patient.

Figure 3:
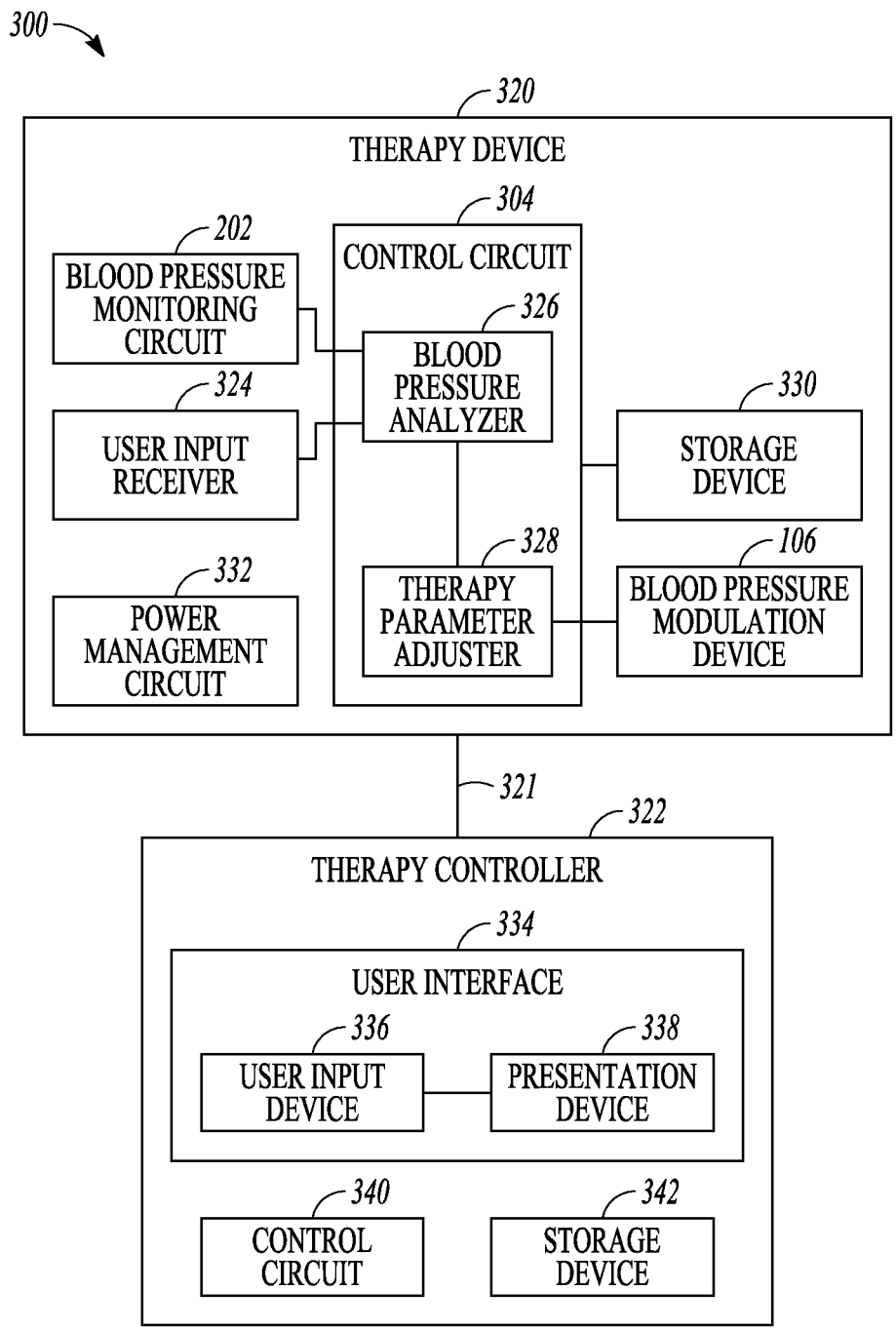
FIG. 3 illustrates another embodiment of a system for modulating blood pressure.

FIG. 3 illustrates an embodiment of a system 300 for modulating blood pressure. System 300 represents a more specific example of system 100 and includes a therapy device 320 and a therapy controller 322. In various embodiments, therapy device 320 and therapy controller 322 can be integrated into a single device or implemented as two or more separate devices. In various embodiments, therapy device 320 can include multiple devices coupled to each other via wired and/or wireless links. In one embodiment, therapy device 320 and therapy controller 322 are integrated into a single device with a user interface, such as for delivering therapy percutaneously or transcutaneously. In embodiments using an implantable device, such as discussed below with reference to FIG. 4, therapy device 320 can be implemented as the implantable device, and therapy controller 322 can be implemented as an external device. In various embodiments, therapy device 320 can includes an implantable device or a front-end device for sensing and therapy delivery, while therapy controller 322 can function as a user controller (for use by a physician or other caregiver or the patient) that include a user interface. In various embodiments, therapy device 320 can includes an implantable device for the therapy delivery and implantable and/or noninvasive sensors communicatively coupled to that implantable device via wired and/or wireless links.

Therapy device 320 can include blood pressure monitoring circuit 202, a user input receiver 324, a control circuit 304, blood pressure modulation device 106, a storage device 330, and a power management circuit 332. User input receiver 324 can receive one or more user commands transmitted from therapy controller 322 via a wireless or wired link 321. In various embodiments, the one or more user commands can include any one or more of the following examples (1)-(3):

(1) A user command for activating or inhibiting the therapy.

(2) A user command indicating a beginning or end of a physical exercise.

(3) A user command indicating a beginning or end of rest (or sleep).

(4) User commands representing feedback from the patient. For example, the feedback can include indication for initiating a calibration of an optimization algorithm executed by control circuit 304.

Control circuit 304 can control delivery of the therapy modulating the blood pressure from blood pressure modulation device 106 using therapy parameters. In one embodiment, control circuit 304 controls delivery of SCS from a neuromodulation device using stimulation parameters.

Control circuit 304 can include a blood pressure analyzer 326 and a therapy parameter adjuster 328. Blood pressure analyzer 326 can receive and analyze the one or more physiological parameters each indicative of the physiological function or state of the patient and optionally one or more functional parameters each indicative of the physical activity or state of the patient, and analyze the received parameters. Therapy parameter adjuster 304 can adjust the therapy parameters an outcome of the analysis. In various embodiments, the analysis can be based on the one or more blood pressure parameters and the one or more activity parameters. The one or more blood pressure parameters include one or more of the one or more physiological parameters received by blood pressure analyzer 326. The one or more activity parameters include one or more of the one or more physiological parameters received by blood pressure analyzer 326 and or the one or more functional parameters received by blood pressure analyzer 326. In some embodiments, blood pressure analyzer 326 can further receive the one or more user commands and include the received one or more user commands in the analysis of the one or more blood pressure parameters and the one or more activity parameters. In various embodiments, control circuit 304 can control delivery of the therapy from blood pressure modulation device 106 using the one or more blood parameters, the one or more activity parameters, and optionally the one or more user commands.

In various embodiments, therapy parameter adjuster 328 can approximately optimize the therapy parameters by executing an optimization algorithm. The optimization algorithm allows the therapy parameters to be set for an approximately optimal therapeutic effect as indicated by the one or more blood pressure parameters and the one or more activity parameters. In some embodiments, the one or more user commands (e.g., user commands representing feedback from the patient) can also be used by the optimization algorithm. In the embodiment in which the therapy includes SCS, the therapy parameters (i.e., stimulation parameters) can include, but are not limited to, electrode configuration, pulse waveform shape, pulse frequency, duty cycle, pulse width, and pulse amplitude, as well as parameters controlling a stimulation paradigm (e.g., kilohertz frequency stimulation, burst stimulation). In various embodiments, therapy parameter adjuster 328 allow for calibration of the optimization algorithm, such as on a periodic or as-needed basis. In one embodiment, the calibration is manually performed by a user such as a physician or other authorized caregiver using therapy controller 322. In one embodiment, the calibration is automatically performed according to a specified schedule, as triggered by a specified event (such as the optimal therapeutic effect falling outside a specified threshold), or in response to a user command entered using therapy controller 322. Exemplary methods for calibration include receiver operating characteristic analysis and psychometric curves. Psychometric curves can be used to correlate parameters measured from signals sensed from the patient with a direct or indirect blood pressure measure as stimulation settings and/or paradigms are shifted. By correlating the blood pressure measure to one or more physiological parameters measured using sensors, the efficiency and accuracy of the therapy system can be improved for delivering therapy when needed, such as when the risk of blood pressure elevation is indicated.

Storage device 330 can store data acquired by therapy device 320. For example, when therapy device 320 is implemented as the implantable device, storage device can be used to store data acquired by the implantable device for transmitted to the external device when needed. Examples of records to be stored storage device 330 include: (i) portions of the one or more blood signals and the one or more activity parameters allowing for trending of the one or more blood pressure parameters as a function of the one or more activity signals (e.g., trending of the change if blood pressure and/or vascular resistance of the patient as a function of the activity level and/or postural change of the patient), (2) record of therapy parameter settings that have been used and basis for each of the settings (e.g., values of the one or more blood pressure parameters and the one or more activity parameters used to optimize each setting), and (3) record of the one or more user commands (e.g., when SCS is temporarily activated or terminated by the patient).

Power management circuit 322 can control a power mode of therapy device 320 or system 300. In various embodiments, power management circuit 322 can place therapy device 320 or system 300 in a low-power mode while the patient is sleeping, as indicated by the activity parameter and/or a user command. For example, the patient is considered to be sleeping when the activity parameter indicates the patient has an activity level under a sleeping threshold specified to indicate sleeping, or when the user command indicates a patient-specified sleeping period. Power management circuit 322 can resume to a normal operation mode in therapy device 320 or system 300 in response to a specified wake-up event. Examples of such wake-up event include expiration of the patient-specified sleeping period, a change in the activity parameter indicating the patient is no longer sleeping, and a change in the one or more physiological parameters exceeding a therapy threshold specified to indicate a need for therapy.

Therapy controller 322 allows the user to receive information from therapy device 320 and control operation of therapy device 320. Therapy controller 322 can include a user interface 334, a control circuit 340, and a storage device 342. User interface 334 can include a user input device 336 and a presentation device 338. User input device 336 can receive information from the patient or the physician or other caregiver, including the one or more user commands. Presentation device 338 can include a display screen and/or other audio and/or visual presentation devices to present information about the patient's blood pressure and/or the operation status and history of therapy device 320. In one embodiment, a touchscreen is used as user input device 858 and presentation device 860. Control circuit 3340 controls operation of therapy controller 322. Storage device 342 can store information transmitted from therapy device 320 as well as information for programming therapy device 320. In various embodiments, system 300 can include one or more storage devices, such as a storage device in the front-end therapy device (e.g., an implantable device), a storage device in a controller/user interface device (e.g., an external device communicatively coupled to the implantable device via a wireless link) and one or more network ("cloud") storage devices, to store data for review by the patient and the physicians and other caregivers as well as researchers.

Figure 4:
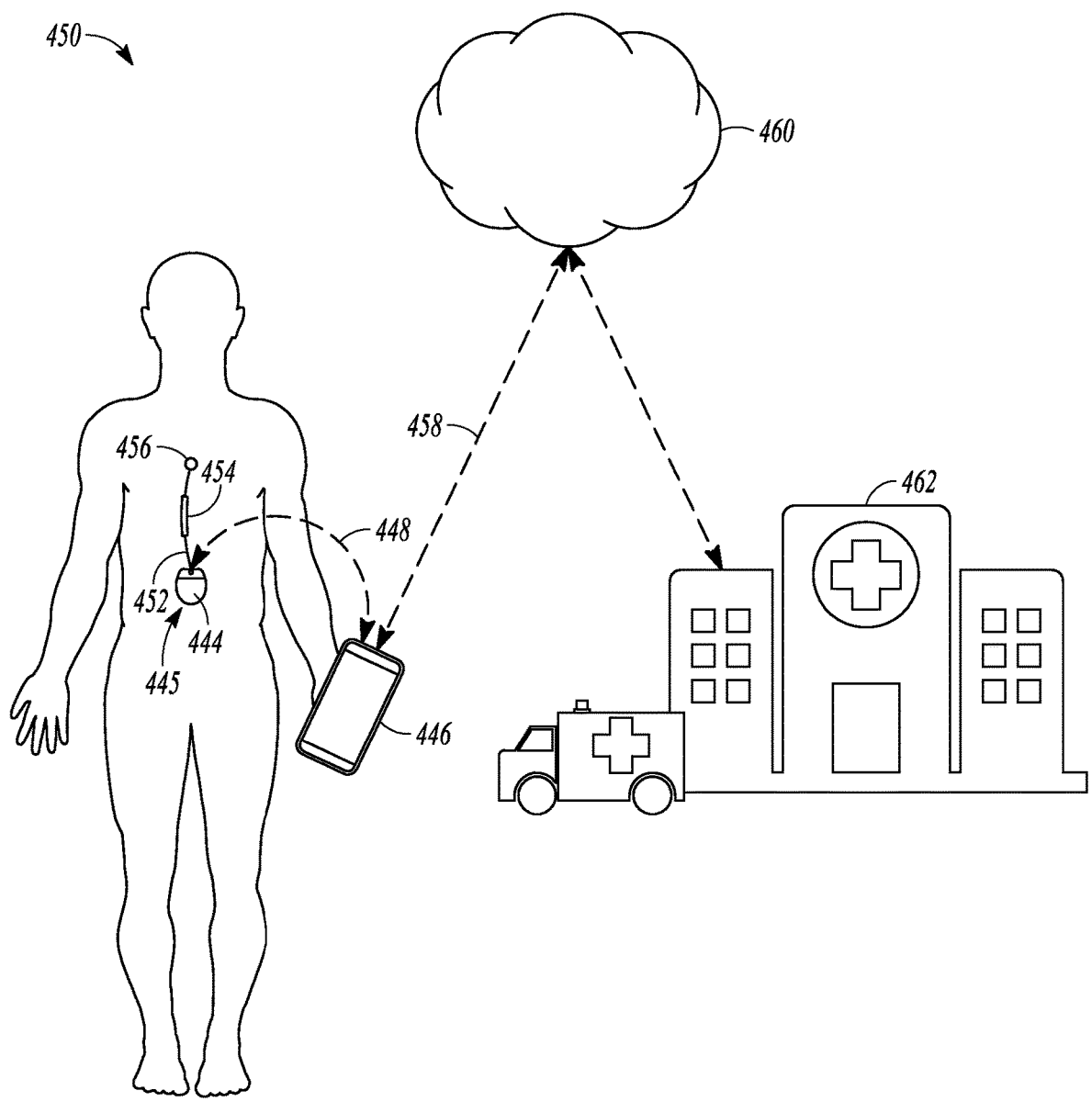
FIG. 4 illustrates an embodiment of an implantable system, such as one in which the system of FIG. 1 or FIG. 3 may be implemented, and portions of an environment in which the implantable system may be used.

FIG. 4 illustrates an embodiment of an implantable system 450 and portions of an environment in which system 450 may be used. System 100 or 300 can be implemented in system 450. System 450 can include an implantable system 445, a portable device 446 communicatively coupled to implantable system 445 via a wireless communication link 448, a network 460 communicatively coupled to portable device 446 via communication link 458, and medical facility 462 communicatively coupled to network 460. Implantable system 445 can include an implantable medical device 444, and an implantable lead or lead system 452 connected to implantable medical device 444. A blood pressure monitoring circuit such as blood pressure monitoring circuit 102 (including its various embodiments) can be contained within implantable medical device 444 or distributed in implantable medical device 444 and portable device 446. Implantable medical device 446 can include a therapy device such as blood pressure modulation device 106 to deliver a therapy that modulate blood pressure. In various embodiments, portable device 446 can be implemented as a dedicated device or in a generic device such as a smartphone, a laptop computer, or a tablet computer. In various embodiments, therapy device 320 can be implemented in implantable system 445, and therapy controller 322 can be implemented in portable device 446 or portable device 446 and network 460.

In the illustrated embodiment, lead or lead system 452 includes an electrode or electrode array 454 and a sensor 456 shown by way of example, but not by way of restriction. In various embodiments, additional one or more electrodes can be incorporated onto implantable medical device 444. In the illustrated embodiment, sensor 456 can represent an embodiment of a sensor (e.g., a heart sound sensor) that is incorporated into lead or lead system 452 and to be positioned in or near the thoracic region. In another embodiment, the sensor can be embedded in implantable medical device 444, which can be an implantable neuromodulator placed in the lumbar region (e.g., for delivering SCS). In various embodiments, each of the one or more physiological sensors and the one or more functional sensors as discussed in this document can be incorporated into lead or lead system 452, included in implantable medical device 444, or implemented as separate device, such as an implantable device or external (e.g., wearable) device, that can communicate with implantable medical device 444 wirelessly via telemetry.

In various embodiments, information related to the patient's blood pressure as well as other information about the patient and/or implantable system 445 can be produced by implantable medical device 444 based on sensed signals and transmitted to portable device 446 via communication link 448. Portable device 446 can selectively relay the received information to network 338 via communication link 458 to be stored, further analyzed, inform the patient's healthcare provider, and/or used to control delivery of the therapy from implantable medical device 444. When the information indicates that the patient needs medical attention, such as when system 450 is unable to automatically adjust the therapy parameters to maintain the patient's blood pressure within a specified range, a notification will be transmitted to medical facility 462 from network 460.

In various embodiments, portable device 446 and one or more devices within network 460 and/or medical facility 462 can allow a user such as a physician or other caregiver and/or the patient to communicate with implantable medical device 444, for example to initialize and adjust settings of implantable medical device 444. For example, portable device 446 may inform the patient the blood pressure and/or other information produced by implantable medical device 644, and allow the patient to turn implantable medical device 444 on and off and/or adjust certain patient-programmable parameters controlling delivery of the therapy.

The sizes and shapes of the elements of system 450 and their locations relative to the patient's body are illustrated by way of example and not by way of restriction. System 450 is discussed as a specific application of the system for modulating blood pressure according to various embodiments of the present subject matter. In various embodiments, the present subject matter may be applied in any type of blood pressure modulation in controlling therapy delivery.

Figure 5:
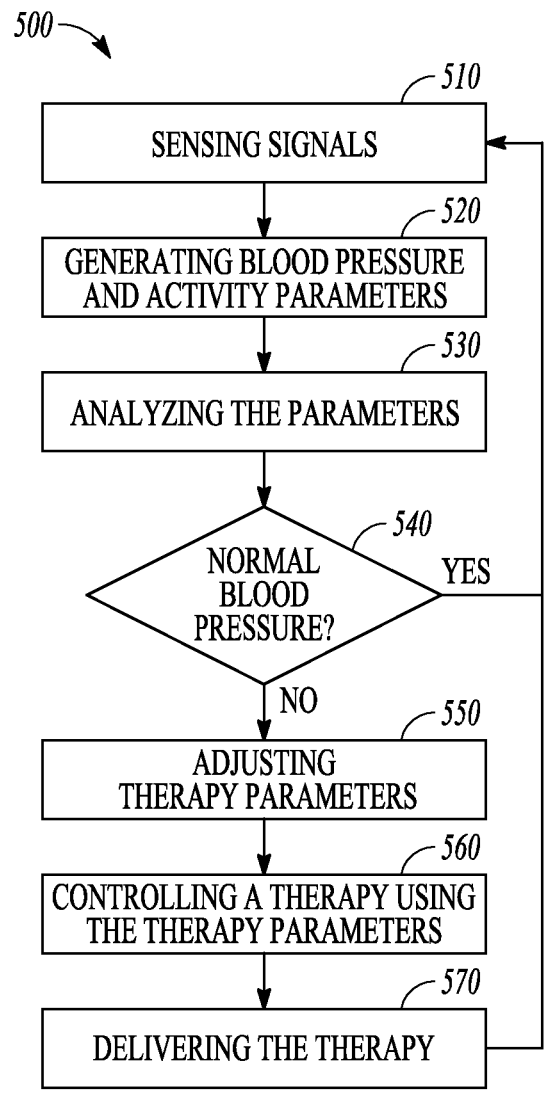
FIG. 5 illustrates an embodiment of a method for modulating blood pressure.

FIG. 5 illustrates an embodiment of a method 500 for modulating blood pressure of a patient. In one embodiment, system 100 or 300 is programmed to perform method 500.

At 510, signals are sensed from the patient. The signals include one or more physiological signals each indicative of a physiological function or state of the patient and optionally one or more functional signals each indicative of a physical activity or state of the patient. The one or more physiological signals indicate a physiological function or state of the patient. The one or more functional signals indicate of a physical activity or state of the patient. Examples of the signals include those sensed using physiological sensor(s) 210 and functional sensor(s) 212 as discussed above with reference to FIG. 2.

At 520, parameters are generated using the sensed signals. The parameters include one or more blood pressure parameters indicative of one or more of a blood pressure or a vascular resistance of the patient and one or more activity parameters indicative of one or more of an activity level or a postural change of the patient. In various embodiments, the one or more blood pressure parameters can be measured from the one or more physiological signals, and the one or more activity parameters can be measured from the one or more physiological signals and/or the one or more functional signals. Examples of the parameters include those produced by parameter generator 216 as discussed above with reference to FIG. 2.

At 530, the parameters generated at 520 are analyzed. In various embodiments, changes in the one or more blood pressure parameters correlated to changes in the one or more activity parameters are analyzed. In some embodiments, one or more user commands are also included in the analysis. Examples of the one or more user commands include those received by user input receiver 324 as discussed above with reference to FIG. 3.

At 540, whether the patient's blood pressure is within a specified normal range is determined using an outcome of the analysis. If the patient's blood pressure is within the specified normal range, the monitoring of the blood pressure may continue without therapy adjustment.

At 550, if the patient's blood pressure is out of the specified normal range, therapy parameters are adjusted. The therapy parameters are used to control a therapy modulating the blood pressure. One example of such therapy includes SCS. In various embodiments, the therapy parameters are approximately optimized by executing an optimization algorithm. The optimization algorithm allows the therapy parameters to be set for an approximately optimal therapeutic effect as indicated by the one or more blood pressure parameters and the one or more activity parameters, and optionally the one or more user commands (e.g., user commands representing feedback from the patient). In various embodiments, the optimization algorithm can be calibrated in response to a need as indicated by the one or more physiological parameters and the one or more functional parameters or in response to a user command for calibration.

At 560, the therapy modulating the blood pressure is controlled using the therapy parameters. At 570, the therapy is delivered to the patient. In various embodiments, method 500 is performed continuously while the patient needs blood pressure modulation and the system performing the method is set to a normal operation mode. The system can be set to a low-power mode when the therapy modulating the blood pressure is not needed, or when a change in the therapy is not needed, such as when the patient is sleeping.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for modulating blood pressure of a patient, the system comprising:
   a blood pressure monitoring circuit configured to sense signals from the patient and generate one or more blood pressure parameters indicative of one or more of a blood pressure or a vascular resistance of the patient and one or more activity parameters indicative of one or more of an activity level or a postural change of the patient using the sensed signals, the blood pressure monitoring circuit including an extravascular physiological sensor configured to indirectly sense the blood pressure using a surrogate of the blood pressure;
   a blood pressure modulation device configured to deliver a therapy for treating hypertension by modulating the blood pressure; and
   a control circuit configured to control the therapy using therapy parameters, to receive the one or more blood pressure parameters and the one or more activity parameters, to analyze changes in the one or more blood pressure parameters that are correlated to changes in the one or more activity parameters, and to adjust the therapy parameters using an outcome of the analysis for delivering the therapy when a risk of blood pressure elevation is indicated.

2. The system of claim 1, wherein the blood pressure monitoring circuit is further configured to receive one or more user commands, and the control circuit is further configured to incorporate the received one or more user commands into the analysis of the changes in the one or more blood pressure parameters that are correlated to the changes in the one or more activity parameters.

3. The system of claim 1, wherein the control circuit is further configured to optimize the therapy parameters by executing an optimization algorithm for an optimal therapeutic effect as indicated by the one or more blood pressure parameters and the one or more activity parameters.

4. The system of claim 3, wherein the control circuit is further configured to allow for calibration of the optimization algorithm in response to the optimal therapeutic effect falling outside a specified threshold or in response to a user command for calibration.

5. The system of claim 4, further comprising a power management circuit configured to control a power mode of the system, the power management circuit configured to place the system in a low-power mode while the patient is sleeping, as indicated by one or more of the one or more activity parameters or a user command indicating a patient-specified sleeping period.

6. The system of claim 4, comprising an implantable medical device configured to be placed within the patient, the implantable medical device including the blood pressure modulation device, the control circuit, and at least a portion of the blood pressure monitoring circuit.

7. The system of claim 6, wherein the blood pressure monitoring circuit comprises an intravascular blood pressure sensor configured to directly sense the blood pressure.

8. The system of claim 1, wherein the extravascular physiological sensor sense at least one of a heart sound sensor configured to sense a heart sound signal, a photoplethysmographic sensor, or an impedance sensor.

9. The system of claim 6, wherein the implantable medical device comprises an implantable neuromodulator, and the blood pressure modulation device is configured to deliver a spinal cord stimulation (SCS).

10. The system of claim 9, further comprising an implantable lead configured to be connected to the implantable neuromodulator, the implantable lead including electrodes configured for delivering the SCS and at least one sensor configured to sense one of the signals from the patient.

11. A method for modulating blood pressure of a patient, including:
    sensing signals from the patient, including sensing an extravascular signal as a surrogate for the blood pressure using an extravascular physiological sensor;
    generating parameters using the sensed signals, the parameters including one or more blood pressure parameters indicative of one or more of the blood pressure or a vascular resistance of the patient and one or more activity parameters indicative of one or more of an activity level or a postural change of the patient;
    analyzing changes in the one or more blood pressure parameters correlated to changes in the one or more activity parameters;
    adjusting therapy parameters using an outcome of the analysis so that a therapy for treating hypertension by modulating the blood pressure is delivered when a risk of blood pressure elevation is indicated;
    controlling the therapy using the therapy parameters; and
    delivering the therapy to the patient.

12. The method of claim 11, further comprising:
    receiving one or more user commands; and
    incorporating the one or more user commands into the analysis of the changes in the one or more blood pressure parameters correlated to the changes in the one or more activity parameters.

13. The method of claim 11, further comprising approximately optimizing the therapy parameters by executing an optimization algorithm, the optimization algorithm allowing the therapy parameters to be set for an approximately optimal therapeutic effect as indicated by the one or more blood pressure parameters and the one or more activity parameters.

14. The method of claim 11, wherein delivering the therapy comprises delivering spinal cord stimulation (SCS) using an implantable medical device.

15. The method of claim 14, wherein sensing the signals comprises sensing the blood pressure using an intravascular blood pressure sensor connected to the implantable medical device.

16. The method of claim 14, wherein sensing the extravascular signal using the extravascular physiological sensor comprises sensing the extravascular signal using an implantable sensor contained in or connected to the implantable medical device.

17. The method of claim 16, wherein sensing the extravascular signal comprises sensing a heart sound signal indicative of heart sounds of the patient.

18. The method of claim 16, wherein sensing the extravascular signal comprises sensing a photoplethysmographic signal.

19. The method of claim 16, wherein sensing the extravascular signal comprises sensing an impedance signal.

20. A non-transitory computer-readable storage medium including instructions, which when executed by a system, cause the system to perform a method for modulating blood pressure of a patient, the method comprising:
    sensing signals from the patient, including sensing an extravascular signal as a surrogate for the blood pressure using an extravascular physiological sensor;
    generating parameters using the sensed signals, the parameters including one or more blood pressure parameters indicative of one or more of the blood pressure or a vascular resistance of the patient and one or more activity parameters indicative of one or more of an activity level or a postural change of the patient;

analyzing changes in the one or more blood pressure parameters correlated to changes in the one or more activity parameters;

adjusting therapy parameters using an outcome of the analysis so that a therapy for treating hypertension by modulating the blood pressure is delivered when a risk of blood pressure elevation is indicated;

controlling the therapy using the therapy parameters; and delivering the therapy to the patient.

* * * * *